United States Patent [19]

Elsberry et al.

[11] Patent Number: 5,711,316
[45] Date of Patent: Jan. 27, 1998

[54] METHOD OF TREATING MOVEMENT DISORDERS BY BRAIN INFUSION

[75] Inventors: Dennis D. Elsberry, New Hope; Mark T. Rise, Monticello; Scott R. Ward, Grove Heights, all of Minn.

[73] Assignee: Medtronic, Inc., Minneapolis, Minn.

[21] Appl. No.: 640,359

[22] Filed: Apr. 30, 1996

[51] Int. Cl.⁶ .................................................. A61B 19/00
[52] U.S. Cl. ........................ 128/898; 604/67; 604/891.1; 128/782
[58] Field of Search ...................... 128/782, 898; 604/890.1, 891.1, 65, 66, 67

[56] References Cited

U.S. PATENT DOCUMENTS

| | | |
|---|---|---|
| 4,692,147 | 9/1987 | Duggan. |
| 5,011,472 | 4/1991 | Aebischer et al. ............. 604/50 |
| 5,031,618 | 7/1991 | Mullett. |
| 5,119,832 | 6/1992 | Xavier. |
| 5,293,879 | 3/1994 | Vonk et al. ...................... 128/782 |
| 5,423,877 | 6/1995 | Mackey. |
| 5,458,631 | 10/1995 | Xavier. |
| 5,474,547 | 12/1995 | Aebischer et al. ............. 604/891.1 |

FOREIGN PATENT DOCUMENTS

| | | | |
|---|---|---|---|
| 0 535 508 A | 9/1992 | Netherlands | 128/782 |
| WO 94/01166 | 1/1994 | WIPO. | |

OTHER PUBLICATIONS

Dill, et al., "Dyskinesias in Rats Following Chemical Stimulation of the Neostriatum", *Texas Reports on Biology and Medicine*, vol. 26, No. 1, Spring, pp. 101–106 (1968).

Kroll, et al., "Increasing Volume of Distribution to the Brain with Interstitial Infusion: Dose, Rather Than Convection, Might Be the Most Important Factor", *Neurosurgery*, vol. 38, No. 4, pp. 746–754 (1996).

Graham, et al., "Injection of Excitatory Amino Acid Antagonists Into the Medial Pallidal Segment of a 1-Methyl-4-Phenyl-1,2,3,6-tetrahydropyridine (MPTP) Treated Primate Reverses Motor Symptoms of Parkinsonism", *Life Sciences*, vol. 47, pp. PL–91–PL–97 (1990).

Crossman, et al., "Experimental Hemiballismus in the Baboon Produced by Injection of a Gamma–Aminobutryric Acid Antagonist into the Basal Ganglia", *Neuroscience Letters*, 20, pp. 369–372 (1980).

Duncan et al., "Thalamic VPM Nucleus in the Behaving Mondey. III. Effects of Reversible Inactivation by Lidocaine on Thermal and Mechanical Discrimination", *Journal of Neurophysiology*, vol. 70, No. 5 pp. 2086–2096 (1993).

Szerb, "Glutamate release and spreading depression in the facia dentata in response to microdialysis with high $K^+$: role of glia", *Brain Research*, 542, pp. 259–265 (1991).

(List continued on next page.)

*Primary Examiner*—V. Millin
*Assistant Examiner*—Kelly R. O'Hara
*Attorney, Agent, or Firm*—Banner & Witcoff, Ltd.

[57] ABSTRACT

The present invention is directed to techniques and apparatus for infusing drugs into the brain to treat movement disorders resulting in abnormal motor behavior. The invention employs an implantable pump and a catheter, the catheter having a proximal end coupled to the pump and a discharge portion for placement adjacent a predetermined infusion site in the brain for infusing therapeutic dosages of the one or more drugs into the brain. The pump is operated to discharge a predetermined dosage of the one or more drugs through the discharge portion of the catheter into the infusion site. A sensor may be used in combination with the implantable pump and catheter, whereby the sensor generates a signal relating to the extent of the abnormal motor behavior. The therapeutic dosage may be regulated in response to the sensor signal so that the dosage is adjusted in response to an increase in the abnormal behavior to decrease the abnormal motor behavior.

29 Claims, 3 Drawing Sheets

OTHER PUBLICATIONS van Horne et al., "Multichannel Semiconductor–Based Electrodes for In Vivo Electrochemical and Electrophysiological Studies in Rat CNS", *Neuroscience Letters*, 120, pp. 249–252 (1990).

Cooper et al., "The Effect of Chronic Stimulation of Cerebellar Cortex on Epilepsy in Man," *The Cerebellum Epilepsy, and Behavior.* Cooper Riklan and Snider ed. Plenum Press, NY. pp. 119–171 (1974).

Godsey et al. "Omnitrode: A Simple Cannula for Chemical and Bipolar Electrical Stimulation", *Physiology and Behavior*, Vo. 8, pp. 773–775, Brain Research Publications Inc. 1972 (Great Britain).

Limousin et al., "Effect on Parkinsonian Signs and Symptoms of Biateral Subthalamic Nucleus Stimulation", *The Lancet*, vol. 345, pp. 91–95 (1995).

Benabid, et al., "Chronic Electrical Stimulation of the Ventralis Intermedius Nucleus of the Thalamus as a Treatment of Movement Disorders", *J. Neurosurg*, vol. 84, 203–214 (1996).

Bobo et al., "Convection–enhanced delivery of macromolecules in the brain", *Proc. Natl. Acad. Sci. USA*, vol. 91, pp. 2076–2080 (1994).

May et al., "Intrastriatal Infusion of Lisuride—a Potential Treatment for Parkinson's Disease? Behavioral and Autoradiographic Studies in 6–OHDA Lesioned Rats", *Neurodegeneration*, vol. 3, pp. 305–313 (1994).

Curtis et al., "A Neurophysiological Analysis of the Effect of Kainic Acid on Nerve Fibres and Terminals in the Cat Spinal Cord", *J. Physiol.*, 368, pp. 99–108 (1985).

Couratier et al., "Cell Culture Evidence for Neuronal Degeneration in Amyotrophic Lateral Sclerosis Being Linked to Glutamate AMPA/Kainate Receptors", *the Lancet*, 341, pp. 265–268 (1993).

Smith, et al., "Serum Antibodies to L–Type Calcium Channels in Patients with Amyotrophic Lateral Sclerosis", *The New England Journal of Medicine*, vol. 327, No. 24, pp. 1721–1728 (1992).

Olson et al, "Intrautaminal Infusion of Nerve Growth Factor to Support Adrenal Medullary Autografts in Parkinson's Disease." Arch. Neurol. 48 pp. 373–381, Apr. 1991.

METHOD OF TREATING MOVEMENT DISORDERS BY BRAIN INFUSION

BACKGROUND OF THE INVENTION

1. Field of the Invention

This invention relates to implantable techniques for infusing a therapeutic agent into the brain, and more particularly, relates to such techniques for treating movement disorders.

2. Description of Related Art

Patients with neurodegenerative diseases or trauma like cerebral infarct or spinal cord injury can have a variety of movement and muscle control problems, like resting, postural, intention or action tremor; dystonia (improper muscle tone); spasticity (undesirable movements, or muscle co-contraction) or dyskinesia (poorly executed movements), involuntary movements like ballismus, chorea and torticollis, (inappropriate movements or limb control). These problems can be chronic, or worse, progressive. They might also have times of relative remission. Such problems are found, at certain stages, for patients with Parkinson's disease, multiple sclerosis, cerebral palsy, secondary to deafferentation pain, post stroke, post apoplexy or anoxia, post head or spinal trauma, post poisoning, cerebellar disease, etc. Dyskinesia also may result from long term usage of Levodopa for Parkinson's patients, or other drugs.

One form of the Dyskinesia is known as Ballism which typically results in violent flinging movements of the limbs. The movements often affect only one side of the body, in which case the disorder is known as Hemiballism.

In patients suffering essential tremor or tremor due to Parkinson's Disease, the predominant symptom of the disordered movement is tremor. Tremor is often subdivided on the basis of whether the trembling of the limb occurs when the limb is at rest or when muscular contraction is occurring.

Besides being caused by degenerative illness or head injury, tremor can be of unknown origin. One syndrome of idopathic tremor is referred to as essential tremor.

Neurosurgeons have been able to diminish the symptoms of the foregoing movement disorders by lesioning certain brain areas.

It is believed that many symptoms of the foregoing motion disorders are due to dysfunction of the basal ganglia. The dysfunction can result in over activity of the output neurons of the ganglia creating excessive inhibition of the thalamus or underactivity of the ganglia resulting in too little inhibition of the thalamus. If there is too little output activity from the basal ganglia or too little inhibition of the thalamus, a condition such as Ballism or Dystonia will result. If there is too much output activity from the basal ganglia (too much inhibition), a condition such as Hypokinesia will result.

Movement disorders such as tremor, Parkinson's disease and Ballism and Dystonia in particular, are in many cases treated by prescription drugs. These drugs in most cases mimic or block the action of one of the transmitter substances active at a synapse somewhere in the basal ganglia. An example is the administration of L-dopa, a precursor to dopamine, for treatment of Parkinson's Disease. The dopamine acts on nerve cells in the neostriatum, compensating for the loss of cells in the Substantia Nigra, pars compacta which have degenerated.

Amyotrophic lateral sclerosis (ALS) is a progressive neurodegenerative disease of unknown origin that results in motor neuron death in the motor cortex and spinal cord producing progressive weakness, paralysis, and respiratory failure and death. Potential causes of ALS include autoimmune response with presence of detectable immunoglobulins in the cerebral spinal fluid (CSF), and the direct binding of IgG to type-1 voltage-gated calcium channels (Smith et. al., 1992). Further, serum from ALS patients is known to be toxic to neuronal cultures, and this neurotoxicity can be blocked by an AMPA/kainate receptor antagonist, i.e. CNQX, (Couratier, et. al., 1993). Motor neurons seem highly sensitive to kainate whereas excitation by NMDA agonists is less toxic (Curtis, et. al., 1985).

Spasticity is defined as a state of excessive muscular tonus (hypertonus) and increased spinal reflexes. This condition exists when the corticospinal pathways have been disrupted. Disruption can occur as a result of stroke causing injury to the fibers as they pass through the internal capsule, a degenerative disorder or physical trauma to the cortex or spinal cord. Loss of this pathway leads to a lack of inhibition of the lower motorneurons which then are more active and responsive to reflexes. In some cases, injury to premotor cortex disrupts the output of the primary motor cortex leading to the similar phenomena. Spasticity presently is treated by infusing baclofen, a GABA agonist, into the intrathecal space to compensate for the loss of descending inhibition.

SUMMARY OF THE INVENTION

A preferred form of the invention can use one or more drugs to treat a movement disorder resulting in abnormal motor response by means of an implantable pump and a catheter having a proximal end coupled to the pump and having a discharge portion for infusing therapeutic dosages of the one or more drugs into the brain. The catheter is implanted in the brain so that the discharge portion lies adjacent to a predetermined infusion site in the basal ganglia or thalamus of the brain. The pump is operated to discharge a predetermined dosage of the one or more drugs through the discharge portion of the catheter into the infusion site. By using the foregoing method, the symptoms of hypokinetic disorders, such as Parkinson's disease, and hyperkinetic disorders, such as Amyotrophic Lateral Sclerosis, Huntington's Disease, Ballism or Dystonia can be alleviated. According to one embodiment of the invention, the one or more drugs can increase excitement of the thalamus or decrease inhibition of the thalamus. According to another embodiment of the invention, the one or more drugs can decrease excitement of the thalamus or increase inhibition of the thalamus.

Another form of the invention uses a sensor in combination with the implantable pump and catheter to administer one or more drugs to treat a movement disorder resulting in abnormal motor behavior. Abnormal motor behavior includes abnormal motor response. In this form of the invention, the sensor generates a signal relating to the extent of the abnormal motor behavior. Control means responsive to the sensor signal regulate the therapeutic dosage so that the dosage is increased in response to an increase in the abnormal motor behavior and is decreased in response to a decrease in the abnormal motor behavior.

By using the foregoing techniques, the symptoms of many movement disorders can be controlled to a degree unattainable by prior art methods or apparatus.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
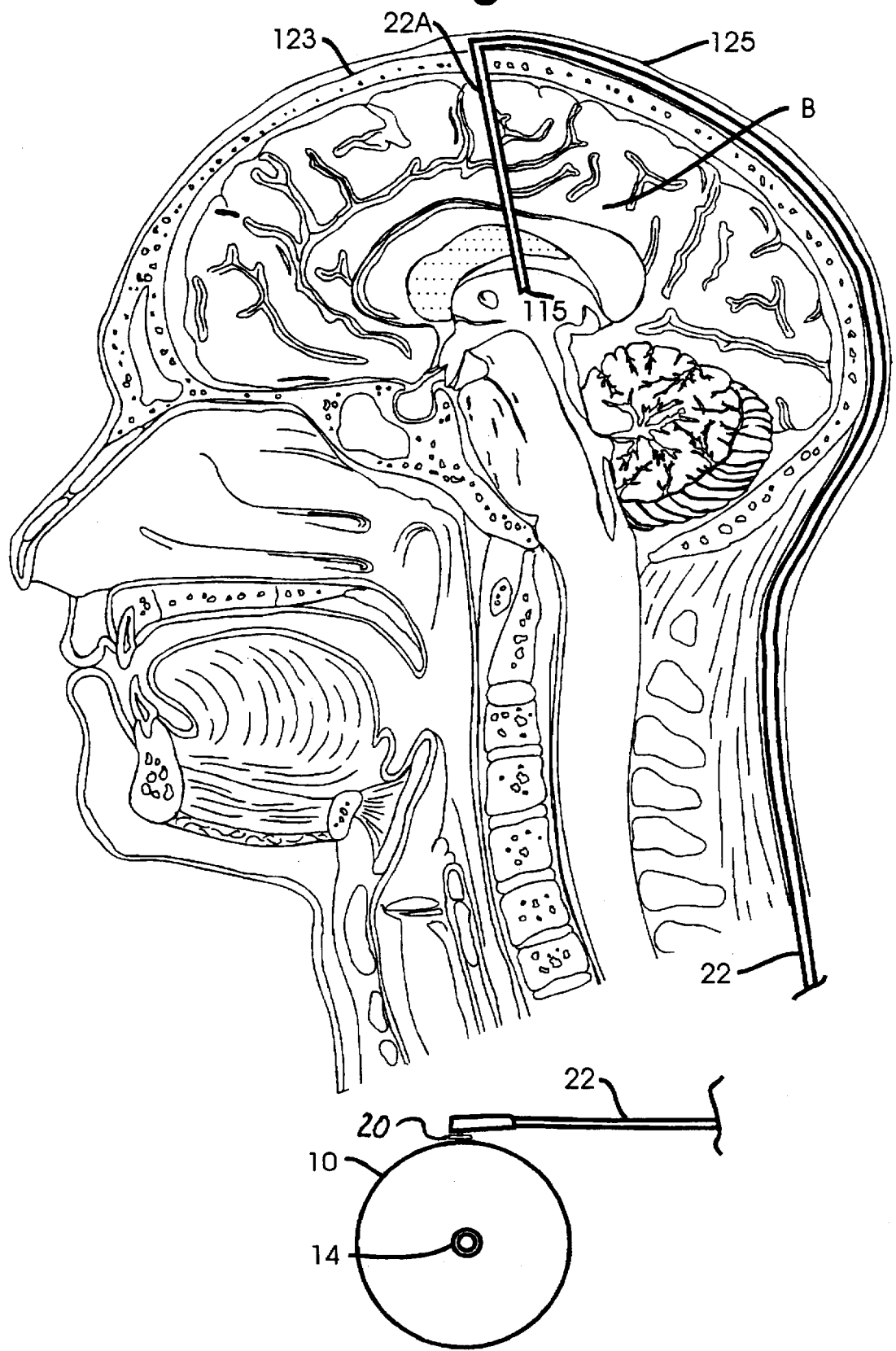
FIG. 1 is a diagrammatic illustration of a catheter implanted in a brain according to a preferred embodiment of the present invention.

Referring to FIG. 1, a system or device 10 made in accordance with the preferred embodiment may be implanted below the skin of a patient. The device has a port 14 into which a hypodermic needle can be inserted through the skin to inject a quantity of a liquid agent, such as a medication or drug. The liquid agent is delivered from device 10 through a catheter port 20 into a catheter 22. Catheter 22 is positioned to deliver the agent to specific infusion sites in a brain (B). Device 10 may take the form of the like-numbered device shown in U.S. Pat. No. 4,692,147 (Duggan), assigned to Medtronic, Inc., Minneapolis, Minn., which is incorporated by reference.

The distal end of catheter 22 terminates in a cylindrical hollow tube 22A having a distal end 115 implanted into a portion of the basal ganglia of the brain by conventional stereotactic surgical techniques. Additional details about end 115 may be obtained from pending U.S. application Ser. No. 08/430,960 entitled "Intraparenchymal Infusion Catheter System," filed Apr. 28, 1995 in the name of Dennis Elsberry et at. and assigned to the same assignee as the present application. Tube 22A is surgically implanted through a hole in the skull 123 and catheter 22 is implanted between the skull and the scalp 125 as shown in FIG. 1. Catheter 22 is joined to implanted device 10 in the manner shown, and may be secured to the device 10 by, for example, screwing catheter 22 onto catheter port 20.

Figure 2:
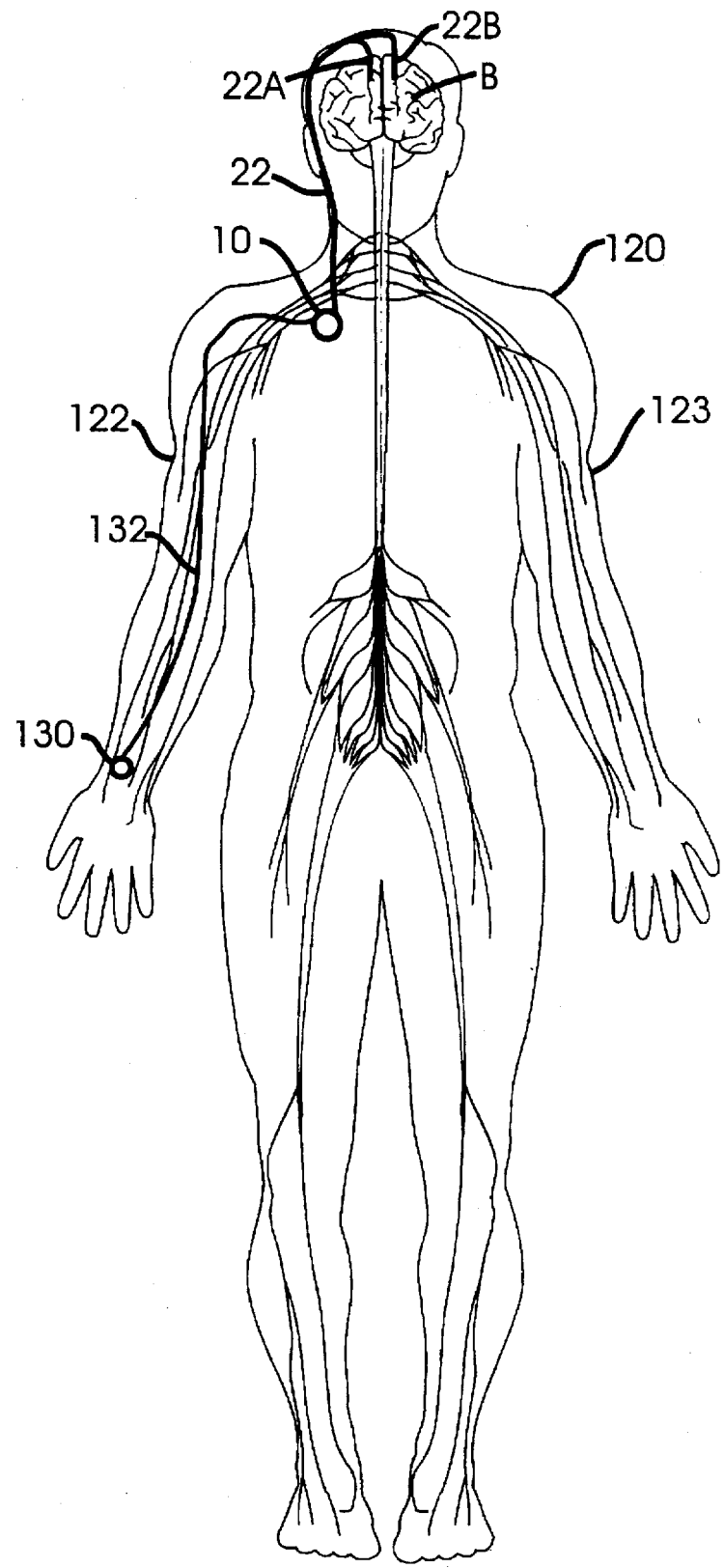
FIG. 2 is a diagrammatic illustration of a portion of the nervous system of the human body in which a preferred form of motion sensor, pump and catheter have been implanted.

Referring to FIG. 2, device 10 is implanted in a human body 120 in the location shown. Body 120 includes arms 122 and 123. Alternatively, device 10 may be implanted in the abdomen.

Catheter 22 may be divided into twin tubes 22A and 22B that are implanted into the brain bilaterally. Alternatively, tube 22B may be supplied with drugs from a separate catheter and pump.

A sensor 130 is implanted into a portion of a patient's body suitable for detecting motion disorder symptoms or abnormal motor behavior. In this specification and claims, abnormal motor behavior includes abnormal motor response. Sensor 130 is adapted to sense an attribute of the symptom to be controlled or an important related symptom. For motion disorders that result in abnormal movement of an arm, such as arm 122, sensor 130 may be a motion detector implanted in arm 122 as shown. For example, sensor 130 may sense three-dimensional or two-dimensional motion (linear rotational or joint motion), such as by an accelerometer. One such sensor suitable for use with the present invention is described in U.S. Pat. No. 5,293,879 (Vonk et al.). Another suitable accelerometer is found in a pacemaker manufactured by Medtronic, Inc., which is described in U.S. application Ser. No. 08/399,072, entitled "Package Integrated Accelerometer", filed Mar. 8, 1995 in the names of James M. Sikorski and Larry R. Larson and assigned to the same assignee as the present invention, which is incorporated by reference. Sensor 130 also may be placed in device 10 in order to detect abnormal movement resulting from the motion disorder being treated.

Sensor 130 also may be capable of detecting gravity direction or motion relative to some object (e.g., a magnet) either implanted or fixed nearby. Sensor 130 also may take the form of a device capable of detecting force in muscles or at joints, or pressure.

Sensor 130 may detect muscle EMG in one, two or more muscles, or in reciprocal muscles at one joint. For such detection, sensor 130 may take the form of a lead with one or more recording electrodes inserted into the muscle of interest.

Brain EEG (e.g., motor cortex potentials recorded above the motor neurons controlling specific muscle groups) also may be detected by sensor 130.

Yet another form of sensor 130 would include a device capable of detecting nerve compound action potentials (e.g., either sensory afferent information from muscle or skin receptors or efferent motor potentials controlling a muscle of interest).

For certain types of patients, sensor 130 may take the form of a device detecting the posture of the patient.

Sensor 130 also may take the form of a device capable of detecting nerve cell or axon activity that is related to the pathways at the cause of the symptom, or that reflects sensations which are elicited by the symptom. Such a sensor may be located deep in the brain. For such detecting, sensor 130 may take the form of an electrode inserted into the internal capsule of the brain. Signals that are received by the sensor may by amplified before transmission to circuitry contained within device 10.

Sensor 130 may electronically transduce the concentration of a transmitter substance present in a particular location of the brain. A paper describing such a sensor is entitled "Multichannel Semiconductor-based Electrodes for In Vivo Electrochemical and Electrophysiological Studies in Rat CNS", by van Horne et at., 120 *Neuroscience Letters* 249–252 (Elsevier Scientific Publishers Ireland Ltd. 1990).

For tremor, the relative motion of a joint or limb or muscle EMG may be productively sensed. Sensing electrical activity of neurons in various locations of the motor circuitry also is helpful. Recording the electrical activity in the thalamus will reveal a characteristic oscillating electrical activity when tremor is present.

For Ballism, Hemiballism or tremor, sensor 130 may take the form of an accelerometer detecting relative motion of a joint or limb or muscle EMG.

For Dystonia, sensor 130 may take the form of a device for detecting relative motion of a joint or limb or muscle EMG.

Figure 3:
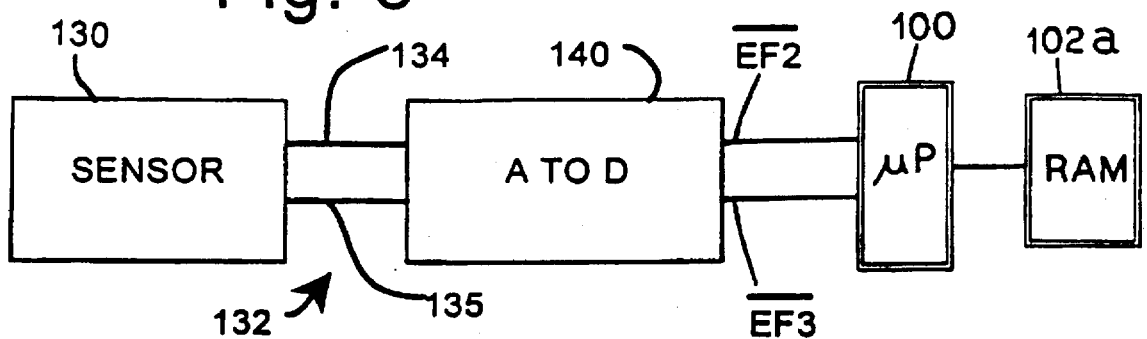
FIG. 3 is a schematic block diagram of a sensor and analog to digital converter circuit used in the preferred embodiment of the invention.

Referring to FIG. 3, the output of sensor 130 is coupled by a cable 132 comprising conductors 134 and 135 to the input of analog to digital converter 140. The output of the analog to digital converter is connected to terminals EF2 BAR and EF3 BAR shown in FIG. 11A of U.S. Pat. No. 4,692,147 ("'147 Patent"). Before converter 140 is connected to the terminals, the demodulator 101 currently shown in FIG. 11A of the 147 Patent would be disconnected.

The present invention may be implemented by providing seven different drug dosages from 0 dosage to a 1.0 ml dosage with 0.1 ml increments between choices. The time interval between dosages can be selected between one and twelve hours in seven choices. This is the same type of dosage and interval described in connection with device 10 shown in the '147 Patent (column 5, beginning at line 63). The seven drug dosages and corresponding time increments may be loaded into RAM 102a (FIG. 11B) of the '147 Patent. The appropriate drug dosage and interval is selected by a computer algorithm that reads the output of converter 140 and makes the appropriate selection.

Figure 4:
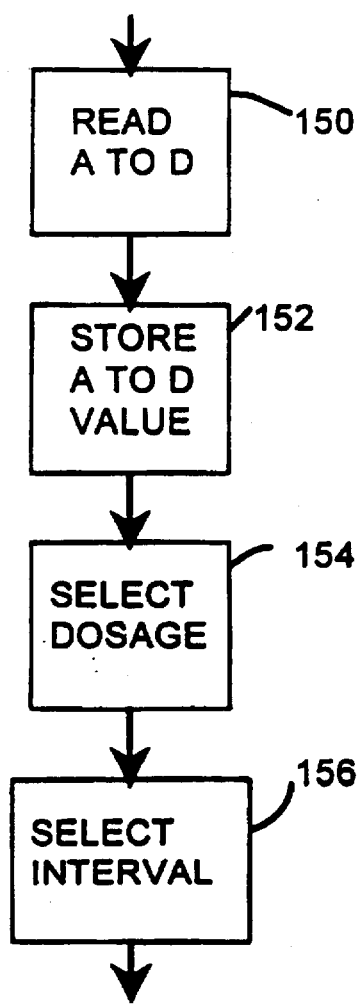
FIG. 4 is a flow chart illustrating a preferred form of a microprocessor program for utilizing the sensor to control the dosage of drug administered to the brain.

One exemplary computer algorithm is shown herein at FIG. 4. Microprocessor 100 included within device 10 reads converter 140 in step 150, and stores one or more values in RAM 102a in step 152. One of seven dosages is selected in step 154, and an appropriate time interval is selected in step 156. The selected dosage and interval of a drug is then delivered through catheter 22 and tube 22A to the basal ganglia of the brain as described in the '147 Patent.

For some types of motion disorders, a microprocessor and analog to digital converter will not be necessary. The output from sensor 130 can be filtered by an appropriate electronic filter in order to provide a control signal for a pump of the type shown in the '147 Patent.

The type of drugs administered by device 10 into the brain depend on the specific location at which distal end 115 of tube 22A is surgically implanted. The appropriate drugs for use in connection with the portion of the basal ganglia or thalamus in which tube 22A terminates, together with the effect of the drug on that portion of the brain for hyperkinetic motion disorders is provided in the following Table I:

TABLE I

| EFFECT | PORTION OF BRAIN | DRUG |
| --- | --- | --- |
| DECREASE EXCITATION | VL THALAMUS | GLUTAMATE ANTAGONIST/ DEGRADING ENZYME |
| INCREASE INHIBITION | VL THALAMUS | GABA AGONIST/ REUPTAKE BLOCKER |
| INCREASE EXCITATION | GPi/SNr | GLUTAMATE AGONIST/ REUPTAKE BLOCKER |
| DECREASE INHIBITION | GPi/SNr | GABA ANTAGONIST/ DEGRADING ENZYME |
| INCREASE EXCITATION | STN | GLUTAMATE AGONIST/ REUPTAKE BLOCKER |
| DECREASE INHIBITION | STN | GABA ANTAGONIST/ DEGRADING ENZYME |
| DECREASE EXCITATION | GPe | GLUTAMATE ANTAGONIST/ DEGRADING ENZYME |
| INCREASE INHIBITION | GPe | GABA AGONIST/ REUPTAKE BLOCKER |
| INCREASE EXCITATION | Neostriatum (Indirect pathway) | GLUTAMATE AGONIST/ REUPTAKE BLOCKER |
| DECREASE INHIBITION | Neostriatum (Indirect pathway) | DOPAMINE ANTAGONIST/ DEGRADING ENZYME |

TABLE I-continued

| EFFECT | PORTION OF BRAIN | DRUG |
| --- | --- | --- |
| DECREASE EXCITATION | Neostriatum (Indirect pathway) | GLUTAMATE ANTAGONIST/ DEGRADING ENZYME |
| DECREASE EXCITATION | Neostriatum (Indirect pathway) | DOPAMINE ANTAGONIST/ DEGRADING ENZYME |

The appropriate drugs for use in connection with the portion of the basal ganglia or thalamus in which tube 22A terminates, together with the effect of the drug on that portion of the brain for hypokinetic motion disorders is provided in the following Table II:

TABLE II

| EFFECT | PORTION OF BRAIN | DRUG |
| --- | --- | --- |
| INCREASE EXCITATION | VL THALAMUS | glutamate agonist/ reuptake blocker |
| DECREASE INHIBITION | VL THALAMUS | GABA antagonist/ degrading enzyme |
| INCREASE INHIBITION | GPi/SNr | GABA agonist/ reuptake blocker |
| DECREASE EXCITATION | GPi/SNr | Glutamate antagonist/ degrading enzyme |
| INCREASE INHIBITION | STN | GABA agonist/ reuptake blocker |
| DECREASE EXCITATION | STN | Glutamate antagonist/ degrading enzyme |
| INCREASE EXCITATION | GPe | glutamate agonist/ reuptake blocker |
| DECREASE INHIBITION | GPe | GABA antagonist/ degrading enzyme |
| INCREASE DOPAMINE | NEOSTRIATUM | Dopamine agonist/ reuptake blocker |

In the foregoing tables I and II, VL Thalamus means ventrolateral thalamus; GPi means internal segment of globus pallidus; SNr means substantia nigra pars reticulata, STN means subthalamic nucleus; and GPe means external segment of globus pallidus.

Typical stereotaxic coordinates based on a normal brain for the portions of the brain described in Tables I and II are identified in the following Table III:

TABLE III

| BRAIN REGION | MEDIAL-LATERAL DIMENSION | DORSAL-VENTRAL DIMENSION | ANTERIOR-POSTERIOR DIMENSION |
| --- | --- | --- | --- |
| VL Thalamus | 0.7 to 1.8 | 1.5 to −0.2 | 0.0 to −1.0 |
| Gpi | 0.5 to 2.0 | 0.5 to −0.7 | 0.7 to 2.0 |
| SNr | 0.5 to 1.5 | −0.6 to −1.5 | 0.7 to −0.7 |
| STN | 0.5 to 2.0 | 0.0 to −1.0 | 0.6 to −1.0 |
| GPe | 1.6 to 2.7 | 1.0 to −1.0 | 2.0 to −1.0 |
| Striatum: | | | |
| Caudate | 0.5 to 2.0 | 1.5 to 3.0 | 1.5 to 3.0 |
| Putamen | 1.2 to 3.3 | 1.5 to −1.0 | 2.5 to −1.2 |

In the foregoing table: the medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to; all dimension are in centimeters.

Examples of specific drugs for the brain infusion sites identified in Tables I and II and preferred ranges of dosages are provided in the following Table IV:

dosage of said one or more drugs into a predetermined infusion site in a brain;

an implantable sensor for generating a signal related to the extent of said abnormal motor behavior; and

TABLE IV

| DESIRED EFFECT | BRAIN TARGET OR TARGETS | DRUG CLASS | SPECIFIC DRUG | DOSING RANGE |
|---|---|---|---|---|
| Decrease Excitation | Ventrolateral Thalamus | Glutamate Antagonists | MK801 (dizocilpine) ketamine Hcl | 1–20 muM  5–50 muM |
| Increase Excitation | Ventrolateral Thalamus | GABA Agonists | baclofen muscinol HBr | 1–10 muM  100–500 muM |
| Increase Excitation | Globus Pallidus Interna/Substantia Nigra reticulata | Glutamate Agonist | D-Cycloserine L-AP4 | 1–10 muM  1–10 muM |
| Decrease Inhibition | Globus Pallidus Interna/Substantia Nigra reticulata | GABA Antagonists | Gabazine Saclofen | 1–50 muM  0.5–25 muM |
| Increase Excitation | Nucleus Subthalamic | Glutamate Agonist | Carboxyphenylglycine L-glutamic acid | 10–500 muM  1–100 muM |
| Decrease Inhibition | Nucleus Subthalamic | GABA Antagonists | Bicuulline picrotoxin | 1–100 muM  10–100 muM |
| Decrease Excitation | Globus Pallidus Externa | Glutamate Antagonist | CNQX AP-3 Dextromethorphan | 1–100 muM  1–10 muM  1–100 muM |
| Increase Inhibition | Globus Pallidus Externa | GABA Agonists | baclofen Muscimol Hbr | 0.1–10 muM  100–500 muM |
| Increase Excitation | Neostriatum (Indirect Pathway) | Glutamate Agonists | cis-Piperidine-2,3-dicarboxylic acid D-Cycloserine | 1–10 muM  1–10 muM |
| Decrease Inhibition | Neostriatum (Indirect Pathway) | Dopamine Antagonist | (+) apomorphine Hcl (−) Sulpiride | 5–20 muM  0.05–1 muM |
| Decrease Excitation | Neostriatum (Indirect Pathway) | Glutamate Antagonist | MCPD dextrorphan tartrate | 0.02–10 muM  1–100 muM |
| Decrease Excitation | Neostriatum (Indirect Pathway) | Dopamine Antagonist | spiperone Hcl haloperidol | 0.1–10 muM  10–100 muM |
| Increase Excitation | Neostriatum | Dopamine Agonist | (−) apomorphine pergolide methanesulfonate | 10–30 muM  1–10 muM |
| Increase Excitation | Motor Cortex | Glutamate Agonists | (+/−)-trans-ACPD L-AP4 | 1–10 muM  1–10 muM |
| Decrease Excitation | Globus Pallidus; Neostriatum | Lidocaine | Lidocaine hydrochloride | 5–20 muM |

In the preceding table, muM means micromolar. Other agents not listed but of the same class could also be used.

Microprocessor 100 within device 10 can be programmed so that a controlled amount of drug can be delivered to the specific brain sites described in Table I. Alternatively, sensor 130 can be used with a closed loop feedback system in order to automatically determine the level of drug delivery necessary to alleviate motor disorder symptoms as described in connection with FIG. 4.

By using the foregoing techniques, motor disorders can be controlled with a degree of accuracy previously unattainable.

Those skilled in that art will recognize that the preferred embodiments may be altered or amended without departing from the true spirit and scope of the invention, as defined in the accompanying claims.

We claim:

1. A system for using one or more drugs to treat a movement disorder resulting in abnormal motor behavior, comprising:
   an implantable pump:
   a catheter having a proximal end coupled to said pump and a discharge portion adapted to infuse a therapeutic dosage of said one or more drugs into a predetermined infusion site in a brain;
   an implantable sensor for generating a signal related to the extent of said abnormal motor behavior; and
   control means responsive to said sensor signal for regulating said therapeutic dosage, whereby the dosage is adjusted in response to an increase in said abnormal motor behavior to decrease said abnormal motor behavior.

2. A system, as claimed in claim 1, wherein said sensor comprises a motion detector.

3. A system, as claimed in claim 1, wherein said sensor comprises means for detecting changes in at least one electrical property of muscle or nerve tissue.

4. A system, as claimed in claim 1, wherein said control means comprises a microprocessor.

5. A system, as claimed in claim 1, wherein said control means comprises an electrical filter.

6. A system, as claimed in claim 1, wherein said movement disorder is a hyperkinetic disorder.

7. A system, as claimed in claim 1 wherein said movement disorder is a hypokinetic disorder.

8. A system for using one or more drugs to treat a movement disorder resulting in abnormal motor behavior, comprising:
   an implantable pump:
   a catheter having a proximal end coupled to said pump and a discharge portion adapted to infuse a therapeutic dosage of said one or more drugs into a predetermined infusion site in a brain;

an implantable sensor for generating a signal related to the extent of said abnormal motor behavior, said sensor being adapted to detect changes in at least one biological characteristic; and control means responsive to said sensor signal for regulating said therapeutic dosage, whereby the dosage is adjusted in response to an increase in said abnormal motor behavior to decrease said abnormal motor behavior.

9. A system, as claimed in claim 8, wherein said at least one biological characteristic includes an electrical property of a muscle.

10. A system, as claimed in claim 9, wherein said sensor comprises a lead having at least one recording electrode adapted for coupling to said muscle.

11. A system, as claimed in claim 8, wherein said at least one biological characteristic includes force in a muscle.

12. A system, as claimed in claim 8, wherein said at least one biological characteristic includes pressure in a muscle.

13. A system, as claimed in claim 8, wherein said at least one biological characteristic includes force in a joint.

14. A system, as claimed in claim 8, wherein said at least one biological characteristic includes pressure in a joint.

15. A system, as claimed in claim 8, wherein said at least one biological characteristic includes an EEG property of said brain.

16. A system, as claimed in claim 15, wherein said EEG property of said brain includes motor cortex potentials above motor neurons controlling a specific muscle group.

17. A system, as claimed in claim 8, wherein said at least one biological characteristic includes nerve compound action potentials.

18. A system, as claimed in claim 17, wherein said nerve compound action potentials include sensory afferent information from muscle or skin receptors.

19. A system, as claimed in claim 17, wherein said nerve compound action potentials include efferent motor potentials controlling a muscle.

20. A system, as claimed in claim 8, wherein said at least one biological characteristic includes a posture of a patient.

21. A system, as claimed in claim 8, wherein said at least one biological characteristic includes nerve cell or axon activity related to at least one pathway at the cause of said abnormal motor behavior.

22. A system, as claimed in claim 21, wherein said sensor comprises at least one electrode adapted for insertion into an internal capsule of said brain.

23. A system, as claimed in claim 8, wherein said at least one biological characteristic includes nerve cell or axon activity that reflects sensations elicited by said abnormal motor behavior.

24. A system, as claimed in claim 23, wherein said sensor comprises at least one electrode adapted for insertion into an internal capsule of said brain.

25. A system, as claimed in claim 8, wherein said sensor electronically transduces a concentration of transmitter substance present at a location of said brain.

26. A system for using one or more drugs to treat a movement disorder resulting in abnormal motor behavior, comprising:

an implantable pump:

a catheter having a proximal end coupled to said pump and a discharge portion adapted to infuse a therapeutic dosage of said one or more drugs into a predetermined infusion site in a brain;

an implantable sensor for generating a signal related to the extent of said abnormal motor behavior, said sensor being adapted to detect movement relative to an object; and control means responsive to said sensor signal for regulating said therapeutic dosage, whereby the dosage is adjusted in response to an increase in said abnormal motor behavior to decrease said abnormal motor behavior.

27. A system, as claimed in claim 26, wherein said object is a magnet.

28. A system, as claimed in claim 27, wherein said magnet is implantable.

29. A system, as claimed in claim 26, wherein said object is implantable.

* * * * *